(12) United States Patent
Sigona

(10) Patent No.: US 9,309,135 B2
(45) Date of Patent: Apr. 12, 2016

(54) METHODS AND APPARATUS FOR DELIVERY SYSTEM FOR WATER ENHANCEMENTS

(75) Inventor: Jon-Andrew V. Sigona, Scottsdale, AZ (US)

(73) Assignee: Perfect Water Technologies, Inc., Scottsdale, AZ (US)

( * ) Notice: Subject to any disclaimer, the term of this patent is extended or adjusted under 35 U.S.C. 154(b) by 944 days.

(21) Appl. No.: 13/472,874

(22) Filed: May 16, 2012

(65) Prior Publication Data

US 2013/0306152 A1 Nov. 21, 2013

(51) Int. Cl.
| | |
|---|---|
| *E03B 7/04* | (2006.01) |
| *C02F 1/68* | (2006.01) |
| *C02F 1/50* | (2006.01) |
| *C02F 1/66* | (2006.01) |
| *C02F 1/76* | (2006.01) |
| *A61K 31/375* | (2006.01) |
| *C05F 11/10* | (2006.01) |
| *C02F 1/44* | (2006.01) |
| *E03C 1/046* | (2006.01) |

(52) U.S. Cl.
CPC .............. *C02F 1/68* (2013.01); *A61K 31/375* (2013.01); *C02F 1/505* (2013.01); *C02F 1/66* (2013.01); *C02F 1/686* (2013.01); *C02F 1/76* (2013.01); *C05F 11/10* (2013.01); *B67D 2210/0001* (2013.01); *C02F 1/441* (2013.01); *C02F 1/688* (2013.01); *C02F 2201/006* (2013.01); *C02F 2303/04* (2013.01); *C02F 2305/14* (2013.01); *C02F 2307/10* (2013.01); *E03C 1/046* (2013.01); *Y10T 137/0318* (2015.04); *Y10T 137/4891* (2015.04)

(58) Field of Classification Search
USPC ...................................................... 137/205.5
See application file for complete search history.

(56) References Cited

U.S. PATENT DOCUMENTS

| | | | | |
|---|---|---|---|---|
| 2,881,781 | A * | 4/1959 | Tavernese et al. | 137/205.5 |
| 4,846,214 | A * | 7/1989 | Strong | 137/268 |
| 5,053,206 | A * | 10/1991 | Maglio et al. | 422/264 |
| 6,913,691 | B2 * | 7/2005 | Holler | 210/198.1 |
| 7,507,334 | B1 | 3/2009 | Sigona | |
| 2004/0055948 | A1 | 3/2004 | Blum et al. | |
| 2007/0012719 | A1 | 1/2007 | Holler | |
| 2008/0020096 | A1 | 1/2008 | Blum et al. | |

\* cited by examiner

*Primary Examiner* — Terry Cecil
(74) *Attorney, Agent, or Firm* — Allen J. Moss; Squire Patton Boggs (US) LLP

(57) ABSTRACT

A delivery system for water enhancements according to various aspects of the present invention is configured to provide a controlled amount of a water enhancement to a water supply. In one embodiment, the delivery system comprises an enhancing device that operates under pressure to provide a controlled rate of diffusion of an enhancing element into the water supply to form an enhanced water supply for use or consumption. The delivery system may also be configured to buffer the enhanced water supply prior to use or consumption.

13 Claims, 4 Drawing Sheets

METHODS AND APPARATUS FOR DELIVERY SYSTEM FOR WATER ENHANCEMENTS

BACKGROUND OF THE INVENTION

There are many commercial options for obtaining water enhanced with vitamins and minerals. However, these options contribute to the production and waste of plastic and glass bottles. In addition, there is no simple delivery system available for dispensing enhanced drinking water and/or enhanced water for the cultivation of plants which can be easily coupled to existing water supplies such as potable water supplies and home reverse osmosis systems commonly found across the world. A challenge faced in providing a system for use in a non-commercial environment is that many enhancement elements possess a high water solubility level, which if not processed properly could result in a product with an unhealthy level of dissolved solute. Another challenge faced in introducing an enhancing element such as vitamins into water, may be the creation of water with an acidic pH. Acidic vitamins such as Vitamin C (ascorbic acid) can be ingested in relatively large dosages without causing harm to human health, but without correct metering into the water, the water may take on an unpleasantly sour taste, cause indigestion, and impact the integrity of metallic system components from exposure to the low (acidic) pH solution.

Another challenge created by the prospect of adding high water solubility elements to a water stream without metering, is a rapid and uncontrolled depletion of the source media. For example, in an unmetered device, a pound of Vitamin C could be dissolved in about a gallon of water. An additional challenge is to ensure that the water to be enhanced is sufficiently pure. Without proper filtering, a number of unpleasant compounds may form as result of exposure to the enhancing element. For example, when chlorinated tap water is mixed with Vitamin C, the chlorine is neutralized but hydrochloric acid (HCL) is formed.

SUMMARY OF THE INVENTION

A delivery system for water enhancements according to various aspects of the present invention is configured to provide a controlled amount of a water enhancement to a water supply. In one embodiment, the delivery system comprises an enhancing device that operates under pressure to provide a controlled rate of diffusion of an enhancing element into the water supply to form an enhanced water supply for use or consumption. The delivery system may also be configured to buffer the enhanced water supply prior to use or consumption.

BRIEF DESCRIPTION OF THE DRAWINGS

A more complete understanding of the present invention may be derived by referring to the detailed description and claims when considered in connection with the following illustrative figures. In the following figures, like reference numbers refer to similar elements and steps throughout the figures.

Figure 1:
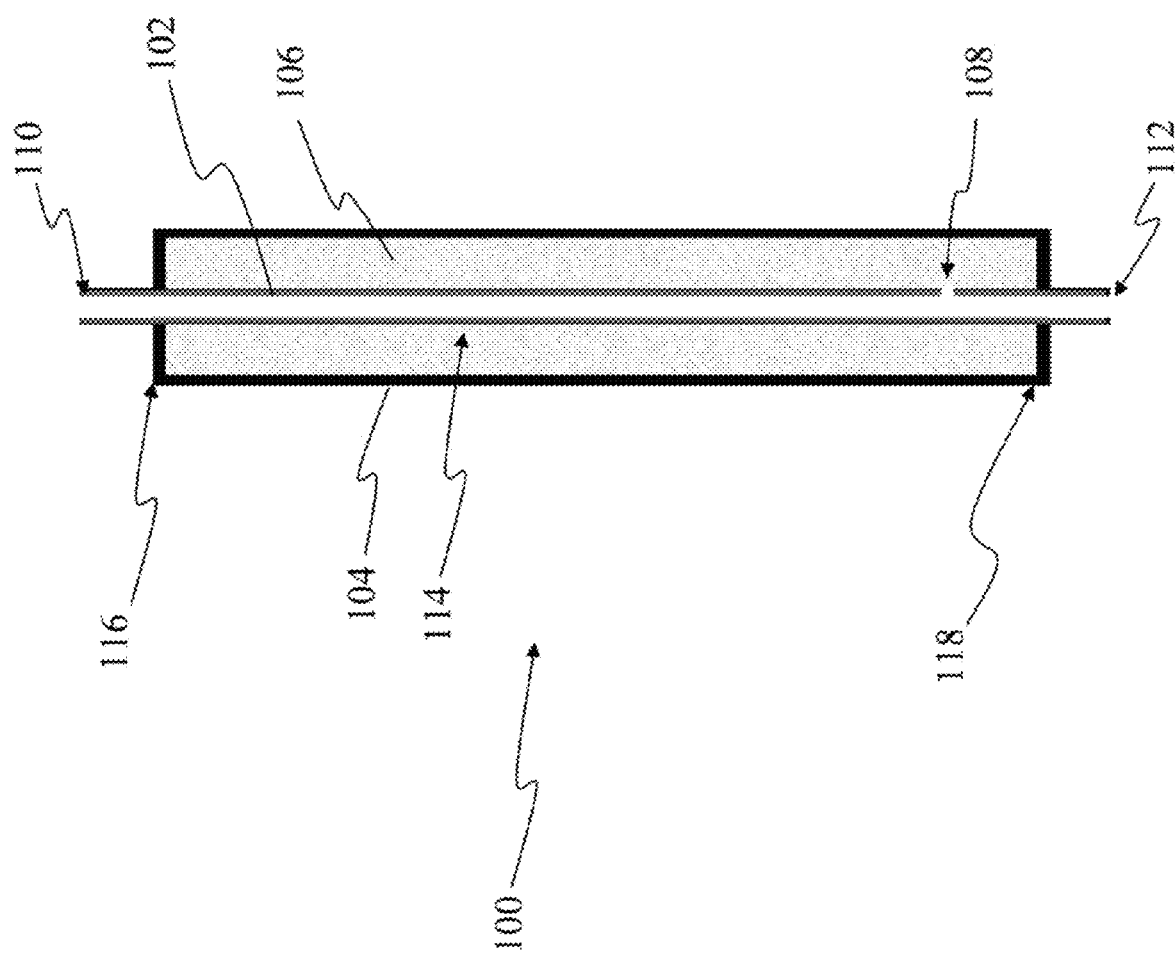
FIG. 1 representatively illustrates an enhancing device in accordance with an exemplary embodiment of the present invention.

Elements and steps in the figures are illustrated for simplicity and clarity and have not necessarily been rendered according to any particular sequence. For example, components that may be coupled together in the manner shown or in a different order are illustrated in the figures to help to improve understanding of embodiments of the present invention.

DETAILED DESCRIPTION OF EXEMPLARY EMBODIMENTS

The present invention may be described in terms of functional block components and various processing steps. Such functional blocks may be realized by any number of components configured to perform the specified functions and achieve the various results. For example, the present invention may employ various types of filters, fittings, valves, fluid conduits, storage equipment, and the like, which may carry out a variety of functions. In addition, the present invention may be practiced in conjunction with any number of processes such as purification of water, reverse osmosis, and carbon filtration, and the system described is merely one exemplary application for the invention. Further, the present invention may employ any number of conventional techniques for removing impurities from water, adding constituents to water, process monitoring, and/or converting fluids from one state to another.

Methods and apparatus for a delivery system for water enhancements according to various aspects of the present invention may operate in conjunction with any suitable water delivery system, water filtration device, and/or water treatment process. Various representative implementations of the present invention may be applied to any system for treating, pressurizing, and/or storing potable or nonpotable water. For example, in one embodiment, the delivery system for water enhancements may be adapted to be retro-fit to, or otherwise be coupled to, and existing reverse osmosis (RO) system intended for installation under a sink or in a commercial vending machine. The delivery system for water enhancements may then receive purified and demineralized flow of water from the RO system and convert the flow of water into an enhanced water flow comprising one or more water soluble elements such as vitamins, soil enhancements, fertilizers, or the like. In another embodiment, the delivery system for water enhancements may be incorporated into a completely integrated RO system suitable for new installations.

The RO system may comprise any suitable system for removing impurities in water such as salt, chlorine, and/or any other elements contained in water. For example, the RO system may comprise a prior art system that is configured to be installed under a sink for residential use and operate at a water pressure of between 40-100 psi. In another embodiment, the RO system may be adapted for larger commercial usage. The RO system may further comprise additional elements such as water lines, a storage tank for storing purified water that is not immediately needed, and a delivery device such as a faucet.

Referring now to FIG. 1, methods and apparatus for a delivery system for water enhancements may comprise an enhancing device 100 adapted to add one or more water soluble elements to a flow of water. The enhancing device 100 may comprise any suitable apparatus or system for dissolving a solute, such as a water enhancement element into an incoming water supply. The enhancing device 100 may also be configured to be coupled downstream from the RO system providing the incoming water supply. In one embodiment, the enhancing device 100 may comprise a sealed housing 104 containing the solute and a water conduit 102 for directing the incoming water supply to the housing 104.

The housing 104 is configured to hold the water enhancement element within a sealed internal volume 106. The housing 104 may comprise any suitable device for containing the water enhancement element and dissolving at least a portion of the water enhancement element into the incoming water supply to form a solution of enhanced water. For example, the housing 104 may comprise a chamber, cartridge, tank, or the like capable of holding water within the internal volume 106 without leaking.

The housing 104 may comprise any suitable material such as plastic, metal, glass, and the like. The housing 104 may also be configured to contain water enhancement element within the internal volume 106 under pressure. For example, in one embodiment, the housing 104 may comprise a polyvinyl composite material capable of safely being exposed to a water supply having a pH level of between 2.0 and 4.0 that is held at an operating pressure of between 40-100 psi.

The water enhancement element is configured to dissolve into a water supply to form the enhanced water. The water enhancement element may comprise any suitable device or media comprising a solute capable of dissolving, dispersing, or otherwise mixing in water to form a solution of water and solute capable of being disposed within the internal volume 106. The solute may comprise any suitable water soluble element or compound such as a vitamin, a fertilizer, a soil enhancer, and/or a water purifying compound. For example, in one embodiment, the water enhancement element may comprise a granular or powdered form of ascorbic acid having a maximum water solubility of about 250 grams per liter (g/L). Accordingly, when the internal volume 106 of the housing 104 is filled with the incoming water supply, the solute will be dissolved until a saturation level of the solute within the water is achieved. In an alternative embodiment, the water enhancement element may comprise a solid block material such that only a surface of the block that is exposed to the incoming water supply may be dissolved. In yet another embodiment, the water enhancement element may comprise a liquid concentrate.

The water enhancement element may be adapted to dissolve into the incoming water supply over a predetermined amount of time before the solute has been completely dissolved. For example, an amount of solute disposed within the housing 104 may be selected according to any suitable criteria such as time or an amount of water to be enhanced. In one embodiment, the amount of solute packaged into the housing 104 may comprise a volume sufficient to enhance 1,000 gallons of water.

The water conduit 102 is configured to direct a supply of unenhanced water to the housing 104 and convey the enhanced water out of the enhancing device 100. The water conduit 102 may comprise any suitable device or element for conveying water into and out of the housing 104 such as a tube, hose, pipe, channel, duct, and the like. The water conduit 102 may comprise any suitable material such as plastic, rubber, glass, metal, or composite material capable of being exposed to varying pH levels.

Referring again to FIG. 1, in one embodiment, the water conduit 102 may comprise an inlet end 110, an outlet end 112, a sealed conduit section 114 disposed between the inlet end 110 and outlet end 112. The water conduit 102 may further comprise a water communication section 108 disposed along a portion of the sealed conduit section 114 that is configured to control fluid communication between the water conduit 102 and the internal volume 106 of the housing 104. The water conduit 102 may be configured to pass through the housing 104 via a first end portion 116 and a second end portion 118 of the housing 104.

The inlet end 110 and outlet end 112 may comprise any suitable device or system for coupling the enhancing device 100 to the incoming water supply. In one embodiment, the inlet end 110 may comprise a section of tubing projecting outward from the first end portion 116 of the housing 104 that is adapted to be coupled to a water line connector such as a compression fitting, a quick connect fitting, and the like. In an alternative embodiment, the inlet end 110 may comprise a connector disposed on the first end portion 116 of the housing 104 that is suitably configured to couple to a water line. In yet another embodiment, the water conduit 102 may comprise a single unit suitably configured to be passed through the first end portion 116 and the second end portion 118 of the housing 104.

The sealed conduit section 114 provides a flow path for the incoming water supply through the housing 104 such that the incoming water supply is not directly exposed to the water enhancement element. The sealed conduit section 114 may be configured to control the rate of diffusion of the water enhancement element into the incoming water supply such that a desired level of enhanced water may be generated for use. For example, the water communication section 108 may be configured to provide an interface in which a rate of diffusion of the solute along a concentration gradient between the saturated enhanced water within the internal volume 106 and the incoming water supply in the sealed conduit section 114 occurs at a preselected rate.

The water communication section 108 may comprise any suitable device or system for allowing bi-directional fluid communication between the internal volume 106 and the sealed conduit section 114 such as a port, an opening, a duct, a valve, or the like. For example, the water communication section 108 may comprise one or more openings in the conduit section of between 0.0100 and 0.1 inches in diameter. In one embodiment, the opening may comprise a substantially round port of approximately 0.0135 inches in diameter. When subjected to a pressurized water supply, water may be forced from the sealed conduit section 114 across the water communication section 108 and into the internal volume 106 of the housing 104 until the internal volume 106 is filled with water. As the incoming water supply is forced into the housing 104, the solute may dissolve into the water until the saturation level of the solute is reached forming an enhanced water supply having a maximum concentration level of the solute.

After the internal volume 106 is filled with water and pressure differentials between the internal volume 106 and the sealed conduit section 114 are equalized, the enhanced water supply within the internal volume 106 may begin to migrate across the water communication section 108 thereby enhancing the incoming water supply in the sealed conduit section 114. For example, in one embodiment where the water enhancement element comprises Vitamin C, the fully saturated level of enhanced water in the internal volume 106 may have a concentration of approximately 100 grams per liter. After a period of time, the diffused amount of enhanced water within the sealed conduit section 114 may comprise a concentration level of approximately 250 milligrams per liter.

The concentration level within the sealed conduit section 114 may be at least partially controlled by increasing or decreasing the size of the water communication section 108. Alternatively, the concentration level of the enhanced water in the sealed conduit section 114 may be adjusted by increasing the number of openings in the water communication section 108. For example, over a period of one to three hours, a single port having a radius of approximately 0.0135 inches may allow a concentration level of Vitamin C within the sealed conduit section 114 of between 200-350 milligrams per liter and a pH level of approximately 2.8-4.0.

The volume of water subject to enhancement by the enhancing device 100 may be controlled by one or more check valves coupled to the enhancement filter 100. Accordingly, the total volume of the incoming water supply that may be enhanced may have a varying level of concentration over time as the solute diffuses across the water communication section 108.

Figure 2:
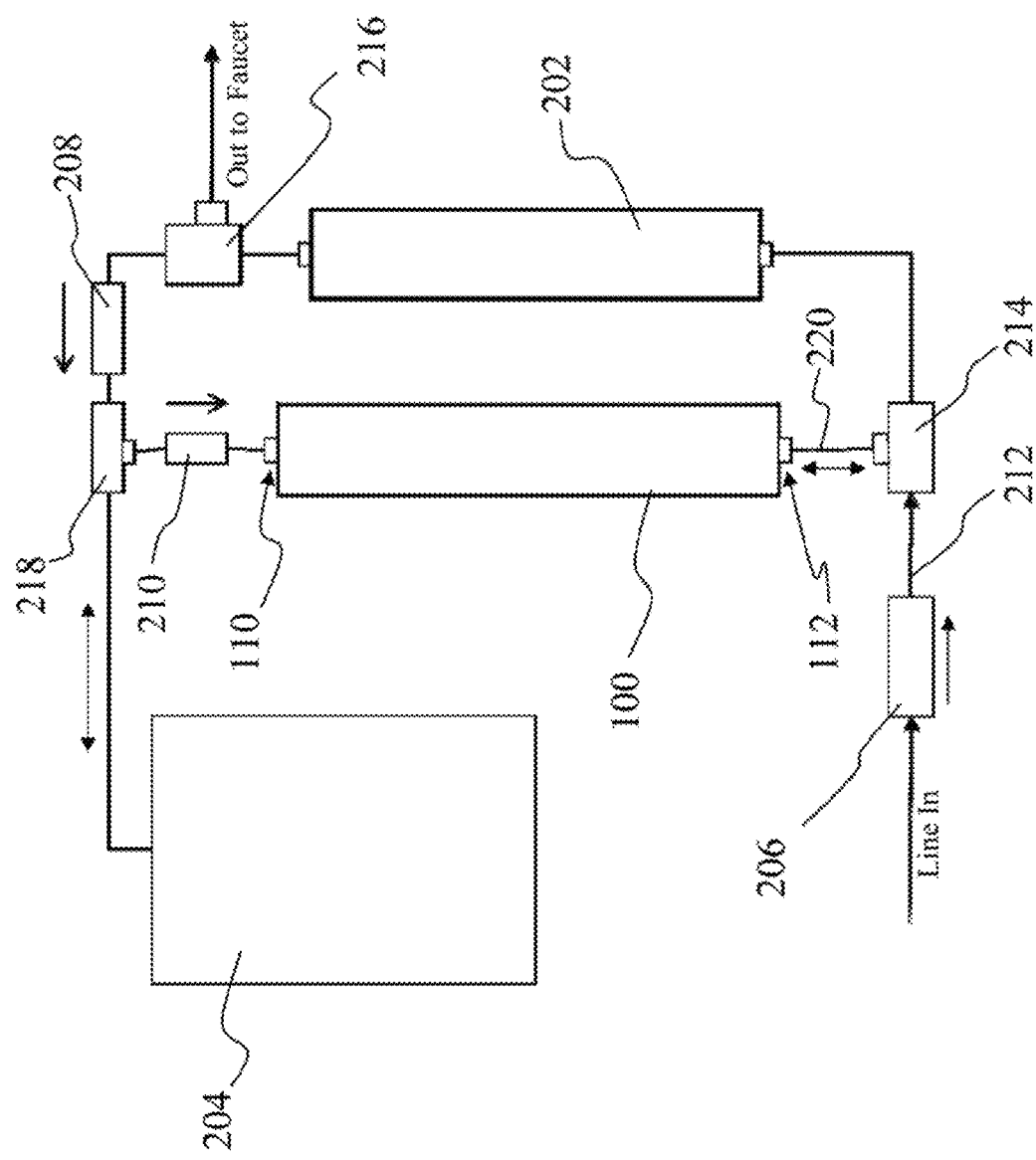
FIG. 2 representatively illustrates the enhancing device coupled to a buffering device in accordance with an exemplary embodiment of the present invention.
Figure 3:
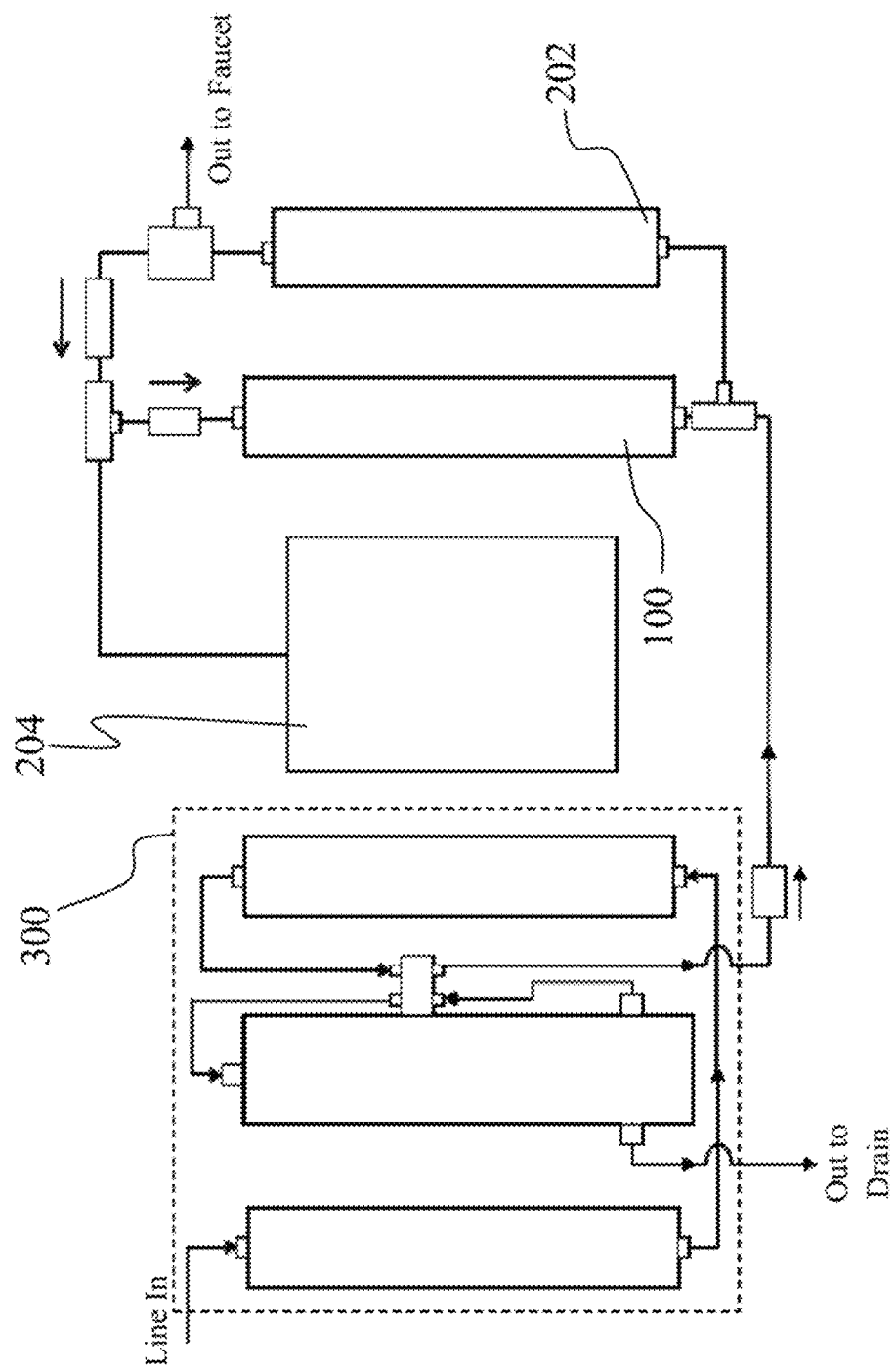
FIG. 3 representatively illustrates a delivery system in accordance with an exemplary embodiment of the present invention.

Referring now to FIGS. 2 and 3, the enhancing device 100 may be coupled to a buffering device 202, a RO system 300, and a storage tank 204. The buffering device 202 may be adapted to adjust the pH of the incoming water supply and/or the enhanced water supply. The storage tank 204 may be configured to store a volume of incoming water supply that has been buffered by the buffering device 202. In addition, a series of check valves 206, 208, 210 may be used to prevent the enhanced water supply from backflowing into the incoming water supply and/or being mixed with the water stored in the storage tank 204.

The buffering device 202 buffers the incoming water supply by raising the pH of the incoming water supply. The buffering device 202 may comprise any suitable system or device for adjusting the pH level of water. For example, in one embodiment, the buffering device may comprise a remineralization filter such as that described by U.S. Pat. No. 7,507,334. The buffering device 202 may be coupled to the enhancing device 100 and the storage tank 204 such that both the incoming water supply and the enhanced water supply are buffered.

The effect of the buffering device 202 on water may depend, at least in part, on what type of water is passed through the buffering device 202. For example, the incoming water supply from the RO system 300 may be slightly acidic as a result of the filtering process comprising a pH level of approximately 6.0-7.0. This slightly acidic incoming water supply may pass through the buffering device 202 and be adjusted to a pH level of approximately 7.0-7.5 prior to being stored under pressure in the storage tank 204.

On command, such as by operation of the faucet, the buffered water from the storage tank 204 may be directed to the enhancing device 100 by a first and second check valve 208, 210. As the buffered water passes into the enhancing device 100, it is mixed with the enhanced water supply as the enhanced water supply is flushed from the enhancing device 100 and directed towards the buffering device 202 by a third check valve 206. As a result of the mixing, the concentration level of the solute in the enhanced water supply may be diluted by the buffered water supply before passing through the buffering device 202 where the enhanced and buffered water is subjected to buffering before being directed to the faucet by the first check valve 208.

In operation, a RO system 300 may generate an incoming water supply that is directed to an enhancing device 100 and a buffering device 202 via an incoming water supply line 212. The incoming water supply may then be diverted between the enhancing device 100 and the buffering device 202 through junction 214. Incoming water that is diverted to the buffering device 202 may be buffered to increase the pH level of the incoming water supply before it is directed to a storage tank 204 by a second junction 216, a first check valve 208, and a third junction 218. The buffering device 202 may utilize a remineralization process to increase the pH of the incoming water supply to between 7.0-7.5.

Incoming water that is diverted to the enhancing device 100 may be contained within the enhancing device 100 by a second check valve 210 coupled to an inlet end 110 of the enhancing device 100. As water pressure begins to build in the enhancing device 100, the incoming water supply may be communicated between an inner chamber and outer chamber of the enhancing device 100. For example, the incoming water supply may enter the enhancing device 100 through an enhancing water line 220 coupled to a bi-directional outlet end 112 of the enhancing device 100.

Water entering the enhancing device 100 may fill a sealed conduit section 114 comprising a water communication section 108. As water pressure builds in the sealed conduit section 114, the incoming water supplied migrates through the water communication 108 and begins to fill a sealed internal volume 106 that comprises a water soluble water enhancement element. As the incoming water supply fills the internal volume 106, the water comes into contact with the water enhancement element which begins dissolving into the incoming water supply.

Over a period of time, the water enhancement element forms an enhanced water supply as a result of an increasing concentration of water enhancement element into the incoming water supply. Eventually, a concentration level of the water enhancement element reaches the maximum solubility level of the water enhancement element and the rate of diffusion slows to zero or substantially zero. For example, in one embodiment, the water enhancement element may comprise ascorbic acid having a maximum solubility of about 250 grams per liter of water.

As a pressure differential across the water communication section 108 is equalized, the enhanced water supply may begin to diffuse along a concentration gradient at the water communication section 108 resulting in enhanced water mixing with the incoming water supply contained within the sealed conduit section 114. The rate of diffusion into the sealed conduit section 114 may be controlled according to the size, shape, or material of the water communication section 108. In one embodiment, the water communication section 108 may comprise an opening of approximately 0.0135 inches. The enhanced water may then form a concentration of enhanced water in the sealed conduit section 114 that is less than that of the internal volume 106.

For example, in the embodiment where the water enhancement element comprises ascorbic acid (Vitamin C), the concentration level of the enhanced water supply in the sealed conduit section 114 may be between 50-400 milligrams per liter of water. The enhanced water supply may be contained within the enhancing device 100 or it may be allowed to migrate beyond the enhancing device 100 while being prevented from diffusing into the entire incoming water supply by the check valves 206, 208, 210.

When a user desires access to the water contained within the system, a faucet may be selectively activated causing a pressure drop. This pressure drop may act on the check valves 206, 208, 210 causing the buffered water in the storage tank 204 to be directed to the inlet end of the enhancing device 100. This water may then mix with and dilute the enhanced water supply in the sealed conduit section 102 thereby lowering the solution level of the Vitamin C in the sealed conduit section 102. For example, the Vitamin C in the sealed conduit section 102 may comprise a concentration level of approximately 250 milligrams per liter. Once diluted with the buffered water supply, the concentration level may drop to approximately 50-100 milligrams of Vitamin C per liter. The diluted, but still enhanced water supply may then be channeled through the buffering device 202 a second time, raising the final product water's pH to approximately 5.5-7.5 resulting in water that approaches tastelessness and is safe for contact with metallic faucets that are low lead complaint.

The amount of enhanced water supplied to the faucet may vary over time as a result of various factors. For example, approximately two liters of an enhanced water supply comprising 75 milligrams of Vitamin C per liter of water with a pH of about 5.5 may be supplied to the faucet before the concentration level begins to drop as a result of the Vitamin C within the sealed conduit section 102 being flushed with the buffered water supply. In addition, it may take approximately an hour before the enhancing device 100 is able to recharge to the desired concentration level of enhanced water.

The resulting enhanced water may vary according to a desired application or water enhancement element. In an alternative embodiment, the enhancing device 100 may be independently coupled to a water line such as a municipal water service or a private well and the water enhancement element may comprise a water soluble fertilizing compound. The concentration level of the enhanced water supply in the internal volume 106 and the sealed conduit section 114 may be determined according to a desired level of fertilization for a given need or crop. Accordingly, the available concentration level of enhanced water and the resulting changes to the incoming water supply's pH level may vary from one application to another.

Figure 4:
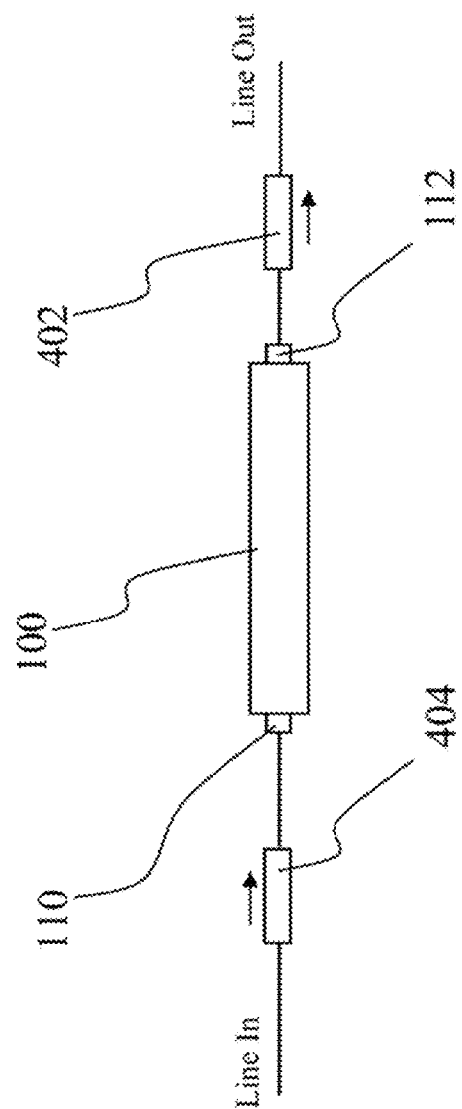
FIG. 4 representatively illustrates the enhancing device without the buffering device in accordance with an exemplary embodiment of the present invention.

For example, referring now to FIG. 4, the inlet end 110 of the enhancing device 100 may be coupled to the incoming water supply line by a check valve 404 and the outlet end 112 may be coupled to a back pressure generating device 402. The incoming water supply may be directed through the check valve 404 to the enhancing device 100 where the incoming water supply is enhanced with the fertilizing compound before continuing through the back pressure generating device 402 to a demand location such as a faucet or hose.

The back pressure generating device 402 generates a pressure force to facilitate water communication between the internal volume 106 of the enhancing device 100 and the sealed conduit 102. The back pressure generating device 402 may comprise any suitable device or system for creating and/or maintaining a desired back pressure on the enhancing device 100 such as a permeate pump, a pressure valve, or the like. In one embodiment, the back pressure generating device 402 may comprise a cyclic pressure valve configured to generate a back pressure on the enhancing device 100 concurrent to a demand for the enhanced water supply. The back pressure generating device 402 may also be configured to maintain a desired pressure range within the enhancing device 100 to avoid large pressure drops when a demand for enhanced water is created. In this way, the enhancing device 100 may be able to provide greater volumes of enhanced water or maintain a more constant concentration level of enhanced water over the course of a demand to the enhanced water.

For example, the back pressure generating device 402 may comprise a valve adapted to open in response to a pressure drop on the line out side of the back pressure generating device 402 and then close in response to a pre-determined pressure drop on the enhancing device 100 side of the back pressure generating device 402. The back pressure generating device 402 may be configured to cycle between the open and closed position allowing the enhanced water supply to flow while preventing a pressure drop within the enhancing device 100 of more than 10-15 psi. By preventing large pressure drops within the enhancing device 100 during a demand such as from a drip irrigation system, it may be possible to maintain the diffusion of enhanced water across the communication point 108 during the demand.

Referring again to FIG. 4, in yet another embodiment, the inlet end 110 of the enhancing device 100 may be coupled to an incoming non-potable water supply line by a check valve 404 and the outlet end 112 may be coupled to a back pressure generating device 402. The incoming non-potable water supply may be directed through the check valve 404 to the enhancing device 100 where the incoming non-potable water supply is enhanced with a purifying compound such as chlorine dioxide, tetraglycine hydroperiodide, sodium dichloroisocyanurate, silver ion, and/or the like to create potable water before continuing through the back pressure generating device 402 to a potable water demand location such as a faucet or hose.

The invention has been described with reference to specific exemplary embodiments. Various modifications and changes, however, may be made without departing from the scope of the present invention. The description and figures are to be regarded in an illustrative manner, rather than a restrictive one and all such modifications are intended to be included within the scope of the present invention. Accordingly, the scope of the invention should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The present invention has been described above with reference to a preferred embodiment. However, changes and modifications may be made to the preferred embodiment without departing from the scope of the present invention. These and other changes or modifications are intended to be included within the scope of the present invention, as expressed in the following claims.

The invention claimed is:

1. A water enhancement apparatus for an incoming water supply, comprising:
    a housing comprising a first end portion and a second end portion defining a sealed internal volume there between, wherein the housing is configured to contain a water soluble enhancement element within the sealed internal volume for providing an enhanced water supply; and
    a water conduit disposed within the sealed internal volume and configured to couple to the incoming water supply, wherein the water conduit comprises:
        a sealed conduit section extending between the first end portion and the second end portion;
        a fluid communication section disposed along a portion of the sealed conduit section, wherein the fluid communication section is configured to allow fluid communication between the sealed internal volume and the water conduit;
        an inlet end coupled to the first end portion and configured to receive the incoming water supply; and
        an outlet end coupled to the second end portion and configured to convey the enhanced water supply away from the sealed housing,
    a buffering system coupled to the first and second end portions of the housing, wherein the buffering system is configured to increase a pH level of the incoming water supply and the enhanced water supply;
    a storage tank coupled to the buffering system and the first end of the housing;
    a first check valve coupled to the second end of the housing and configured to prevent the enhanced water supply from backflowing into the incoming water supply;
    a second check valve coupled to the buffering system and configured to allow buffered water to enter the storage tank; and
    a third check valve coupled to the first end of the housing and configured to allow buffered water to flow into the inlet end of the water conduit.

2. A water enhancement apparatus according to claim 1, wherein the fluid communication section comprises a port configured to allow bi-directional fluid communication between the sealed internal volume and the water conduit.

3. A water enhancement apparatus according to claim 2, wherein the port is configured to control a solution level of the enhanced water supply.

4. A water enhancement apparatus according to claim 3, wherein:
    the water soluble enhancement element comprises vitamin C; and
    the port is configured to provide a solution level of approximately 50 to approximately 400 milligrams per liter of enhanced water supply to enter the water conduit.

5. A water enhancement apparatus according to claim 2, wherein the water soluble enhancement element comprises a water purifier adapted to convert non-potable water into potable water.

6. A water enhancement apparatus according to claim 1, wherein the buffering system is adapted to buffer the incoming water supply to a pH level of approximately 6.5 to approximately 8.0.

7. A water enhancement apparatus according to claim 1, further comprising a back pressure generating device configured to generate a back pressure on the outlet end of the water conduit.

8. A water enhancement system for enhancing an incoming water supply line from a reverse osmosis water purifying device, comprising:
    a buffering device comprising:
        an inlet end coupled to receive a water flow from the incoming water supply line and an enhanced water line;
        an outlet end coupled to convey the water flow to an outlet water line; and
        a buffering element disposed between the inlet end and the outlet end, wherein the buffering element is configured to increase a pH level of the water flow prior to the water passing through the outlet end; and
    an enhancing device comprising:
        a housing defining a sealed internal volume, wherein the housing is configured to contain a water soluble enhancement element for providing an enhanced water supply;
        a receiving end disposed at a first end portion of the housing and configured to receive the water flow from the buffering device;
        an enhancement end disposed at a second end portion of the housing and configured to convey the enhanced water supply to the enhanced water line;
        a water conduit extending between the receiving end and the enhancement end within the sealed internal volume, wherein the water conduit comprises a sealed conduit section configured to provide:
            a fluid flow path between the receiving end and the enhancement end for the water flow; and
            fluid communication between the sealed internal volume and the water conduit;
    a storage tank coupled to the buffering device and the enhancing device;
    a first check valve coupled to the dual communication end of the enhancing device and configured to prevent the enhanced water supply from backflowing into the incoming water supply line;
    a second check valve coupled to the buffering device and configured to allow buffered water to enter the storage tank; and
    a third check valve coupled to the receiving end of the enhancing device and configured to allow buffered water from the buffering device and the storage tank to flow into the receiving end of the enhancing device.

9. A water enhancement system according to claim 8, wherein the sealed conduit section comprises a fluid communication section configured to allow bi-directional fluid communication between the sealed internal volume and the water conduit.

10. A water enhancement system according to claim 9, wherein the fluid communication section is configured to control a solution level of the enhanced water supply.

11. A water enhancement apparatus according to claim 10, wherein:
    the water soluble enhancement element comprises vitamin C; and
    the fluid communication section is configured to provide a solution level of approximately 50 to approximately 400 milligrams per liter of enhanced water supply to enter the water conduit.

12. A water enhancement system according to claim 8, wherein the enhancement end is further coupled to receive the water flow from the incoming water supply line.

13. A water enhancement system according to claim 8, wherein the buffering system is adapted to buffer the incoming water supply to a pH level of approximately 6.5 to approximately 8.0.

* * * * *